United States Patent [19]

Jaeger

[11] Patent Number: 5,905,213
[45] Date of Patent: May 18, 1999

[54] LIQUID SAMPLER HAVING CONNECTING DEVICE

[76] Inventor: Ben E. Jaeger, 50 Hunter La., Yorkville, Ill. 60560

[21] Appl. No.: 09/115,285

[22] Filed: Jul. 14, 1998

[51] Int. Cl.⁶ ....................................................... G01N 1/00
[52] U.S. Cl. ........................................................ 73/863.85
[58] Field of Search ........................... 73/863.81, 863.82, 73/863.85, 863.86, 866.5

[56] References Cited

U.S. PATENT DOCUMENTS

| | | | |
|---|---|---|---|
| 3,007,340 | 11/1961 | Kraftson | 73/865.5 |
| 4,147,062 | 4/1979 | Jaeger . | |
| 4,262,533 | 4/1981 | Jaeger . | |
| 4,472,977 | 9/1984 | Lynn . | |
| 4,475,410 | 10/1984 | Jaeger . | |
| 4,628,732 | 12/1986 | Makinen . | |
| 4,744,255 | 5/1988 | Jaeger . | |
| 4,852,412 | 8/1989 | Hill | 73/863.85 |
| 5,747,708 | 5/1998 | Weiberth | 73/863.81 |

*Primary Examiner*—Robert Raevis
*Attorney, Agent, or Firm*—Juettner Pyle Piontek & Underwood

[57] ABSTRACT

A sampling apparatus is characterized by a sampler housing coupled to a movable valve of a connecting device. The housing and the movable valve have bores that are in communication and axial alignment. One end of the valve bore communicates with the interior of a liquid containing vessel. A plunger is in the housing bore and has an annular recess intermediate its ends. The plunger is reciprocated in the housing and valve bores to project the recess into the vessel to receive a sample of liquid therein, and to then retract the recess from the vessel and through the valve and housing bores to a sample collection point in the housing. Plunger seals maintain a liquid seal between the vessel interior and the sample collection point in the housing during reciprocation of the plunger. The valve is movable between an operative position where the one end of its bore communicates with the vessel interior and an inoperative position where the one end of its bore is out of communication with the vessel interior. Movement of the valve to the inoperative position enables the sampler housing to be disconnected from the valve for maintenance, repair or replacement without allowing liquid to escape from the vessel through the valve bore.

12 Claims, 3 Drawing Sheets

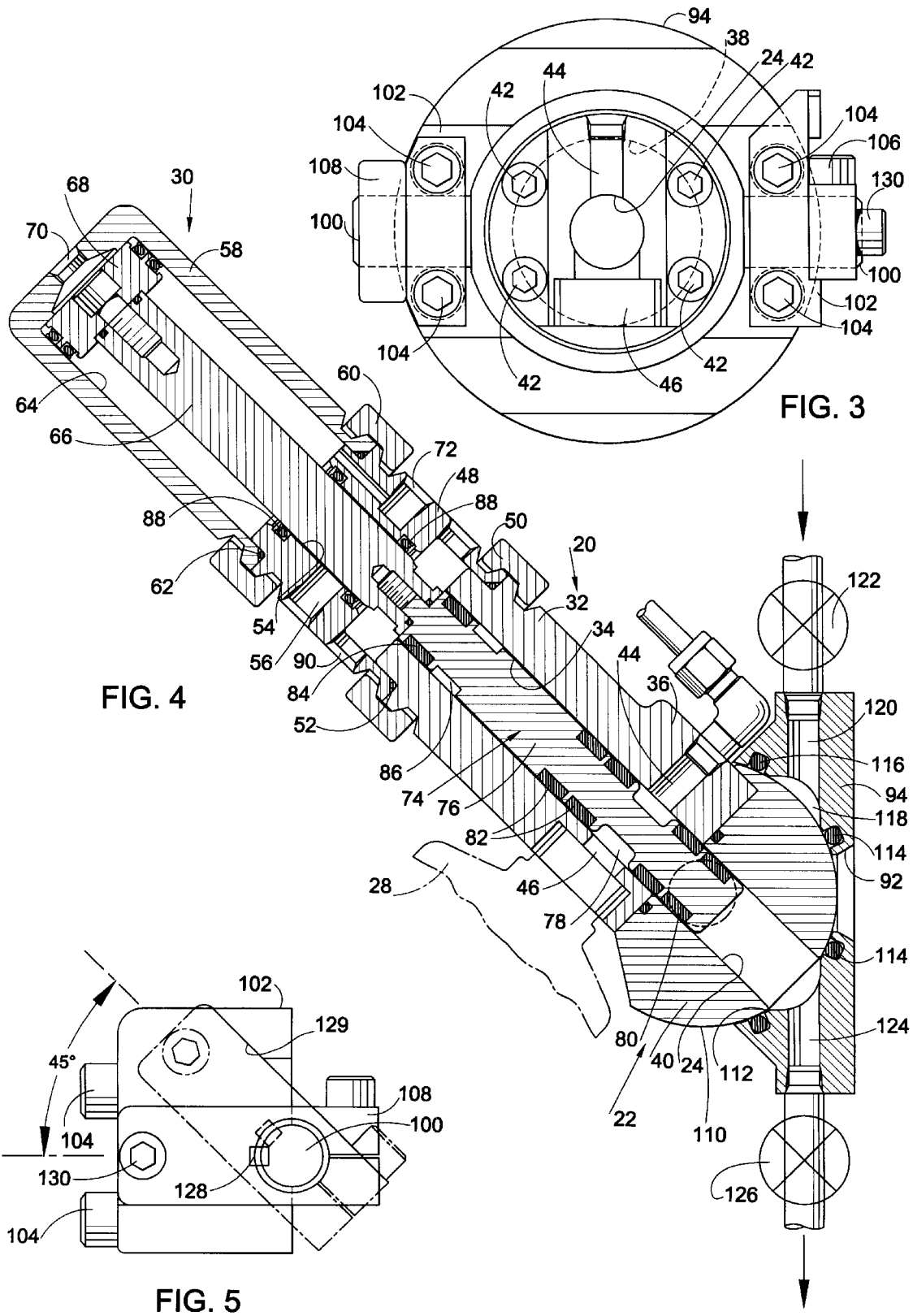

5,905,213

LIQUID SAMPLER HAVING CONNECTING DEVICE

BACKGROUND OF THE INVENTION

The present invention relates to apparatus for extracting samples of liquid from flow lines or tanks.

Certain manufacturing operations require that the immediate or overall composition of a liquid flowing through a pipe or contained within a vessel or tank be monitored. Such monitoring ordinarily is accomplished with sampling apparatus, which takes samples of liquid from a main body of the liquid. Where a composite sample of the liquid is required, the sampler may be periodically operated to withdraw a series of small, measured amounts of the liquid as it passes a sampling point. The small, measured amounts are collected and admixed to form a representative sample of the total volume of liquid.

Other uses for samplers are in on-line analysis applications, in which the immediate composition of a liquid must be determined. For this application, the individual samples of liquid are not collected as a composite sample, but instead are received and analyzed separately.

Four exemplary types of sampling apparatus of the type contemplated by the prior art are disclosed in U.S. Pat. Nos. 4,147,062, 4,262,553, 4,475,410 and 4,744,255, issued to Ben E. Jaeger, the present inventor, and the teachings of all of which are incorporated herein by reference. Sampling apparatus of the type disclosed in said patents is attached to an access line to a pipe or vessel containing the body of liquid, so that a liquid sample receiving recess in a plunger of the sampler can be extended through the access line and an aperture in the pipe or vessel into the main body of liquid for receiving a liquid sample in the recess. The plunger is then retracted to deliver the liquid sample to a collection point in the sampler.

A disadvantage of the foregoing arrangement is that the sampler is always directly coupled through the access line with the body of liquid from which samples are to be taken, so that replacement, repair or maintenance of the sampling apparatus cannot be carried out without disturbing the body of liquid itself. This is because the sampler cannot simply be disconnected from the access line without causing uncontrolled escape of liquid from the main body through the access line. Consequently, before removal of the sampler, the main body of liquid must be interrupted, at least in the vicinity of the access line.

U.S. Pat. No. 4,628,732, issued Dec. 16, 1986 and the teachings of which are incorporated herein by reference, teaches a valve type connecting device for coupling a passive measuring instrument to a process having a parameter to be measured. The parameter may comprise temperature, density, pH value, consistency or some other characteristic of the process. The connecting device has a movable valve member through which a bore extends. The valve member is movable between positions placing the bore in and taking the bore out of communication with the process. The measuring instrument is connected to and received within the bore through the valve member. When the valve member is positioned to place the bore in communication with the process, the measuring instrument can be extended through the bore and into the process to measure a parameter of the process. To replace or repair the measuring instrument, the measuring instrument is retracted from the process and the valve member is moved to the position taking its bore out of communication with the process. The measuring instrument can then be disconnected from the valve member and removed from the bore without resulting in process escaping through and out of the bore.

While the apparatus of said U.S. Pat. No. 4,628,732 can couple a measuring instrument to a process having a parameter to be measured, the parameter must be of a type that is capable of being measured by an instrument that remains stationary in contact with the process, since the apparatus does not accommodate removal of a sampled portion of the process.

OBJECTS OF THE INVENTION

An object of the present invention is to provide a liquid sampler that can be removed from connection with a pipe or vessel carrying a main body of liquid to be sampled, without disturbing the main body of liquid.

Another object is to provide such a sampler that includes a connecting device for selectively placing the sampler into and out of communication with the main body of liquid to permit the sampler to be removed for replacement or repair without disrupting the body of liquid.

A further object is to provide such a sampler in which the connecting device comprises a valve member movable between one position placing the sampler in communication with the main body of liquid and another position placing the sampler out of communication with the main body of liquid.

Yet another object is to provide such a sampler in which the connecting device, when placing the sampler in communication with the main body of liquid, accommodates extension of a sampling recess in a plunger of the sampler into the main body of liquid for receiving in the recess a liquid sample of measured volume for removal to a sampling point remote from the main body of liquid.

SUMMARY OF THE INVENTION

The invention provides a sampling apparatus that comprises a liquid sampler operable to obtain discrete samples of liquid from a body of liquid in a vessel, and a connecting device for coupling the liquid sampler to the vessel at an aperture in the vessel. The liquid sampler is releasably attached to the connecting device, and the connecting device is operable between a first position where the liquid sampler is in communication with the liquid in the vessel through the aperture and a second position where the liquid sampler is out of communication with the aperture and the liquid in the vessel. When the connecting device is in the second position, the liquid sampler is detachable from the connecting device without occurrence of an escape of liquid from the vessel.

In a preferred embodiment of the invention, a bore extends through the connecting device and the liquid sampler communicates with one end of the bore when the sampler is attached to the connecting device. An opposite end of the bore is in communication with the aperture in the vessel when the connecting device is in the first position and is out of communication with the aperture when the connecting device is in the second position. The connecting device includes a body having an opening therein, which body is adapted to be coupled to the vessel with the opening at the aperture to the vessel. A valve member is carried by the body and movable relative thereto, and the connecting device bore extends through the valve member. The liquid sampler is releasably attached to the valve member in communication with the one end of the bore, and the valve member is movable to place the opposite end of the bore into communication with the aperture in the vessel when the connecting device is in the first position, and is movable to place the opposite end of the bore out of communication with the aperture when the connecting device is in the second position. The liquid sampler is movable with the valve member when the connecting device is operated between its first and second positions.

The foregoing and other objects, advantages and features of the invention will become apparent upon a consideration of the following detailed description, when taken in conjunction with the accompanying drawings.

BRIEF DESCRIPTION OF THE DRAWINGS

FIG. 3 is a side elevation view taken substantially along the lines 3—3 of FIG. 2;

FIG. 4 is a cross sectional side elevation view showing the sampler and connecting device moved to a position where the sampler is out of communication with the body of liquid to be sampled, and FIG. 5 is a side elevation view of a portion of a lock arm at the forward end of the sampler.

DETAILED DESCRIPTION

The invention comprises a sampling apparatus that includes a liquid sampler and a connecting device. The sampler is indicated generally at 20 and the connecting device generally at 22. A bore or passage 24 extends through the connecting device, by means of which the sampler can be placed into communication with a main body of liquid within a pipe or vessel 26 for obtaining a discrete liquid sample of measured volume from the main body of liquid.

Figure 1:
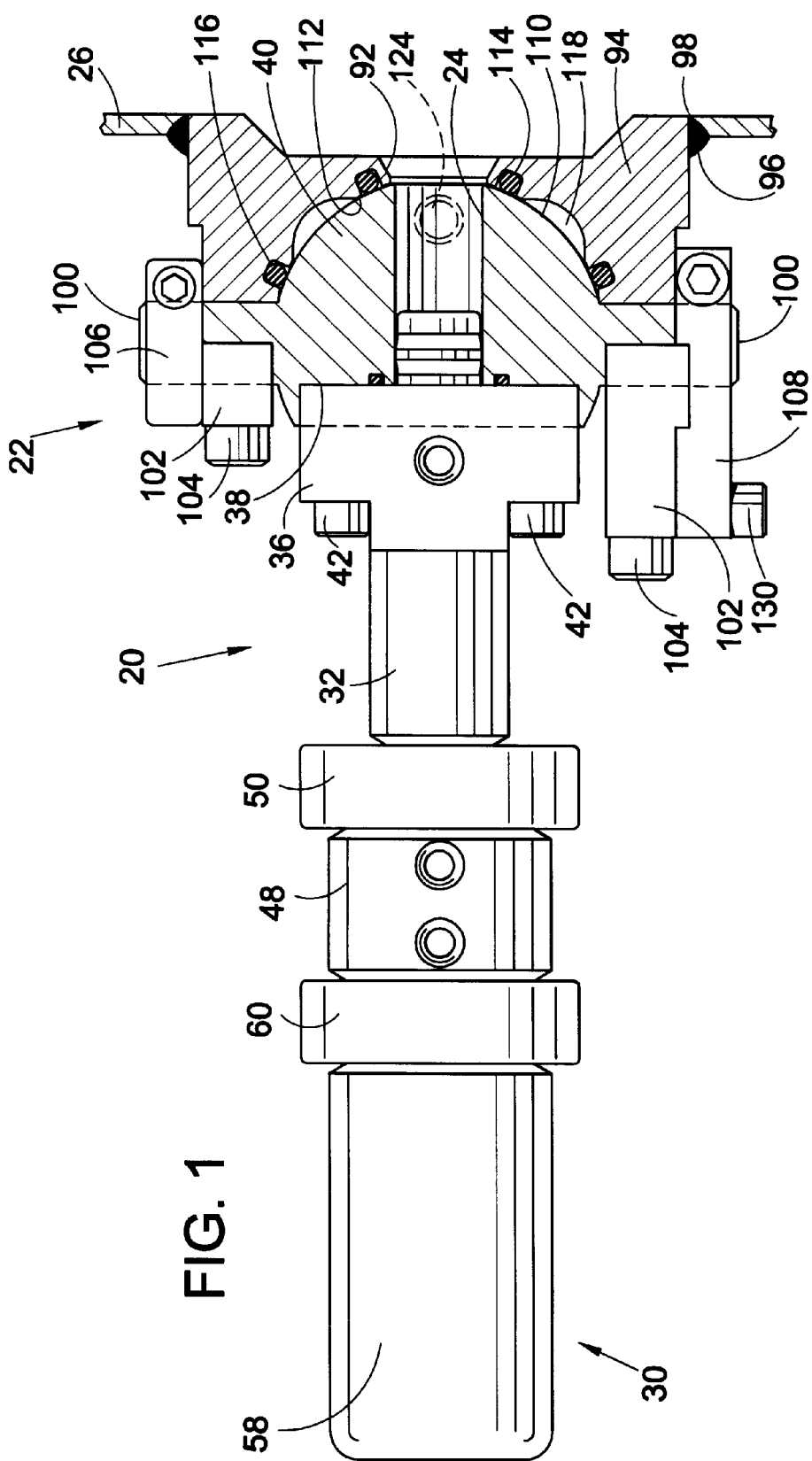
FIG. 1 is a top plan view of a sampler having a connecting device according to the teachings of the present invention.
Figure 2:
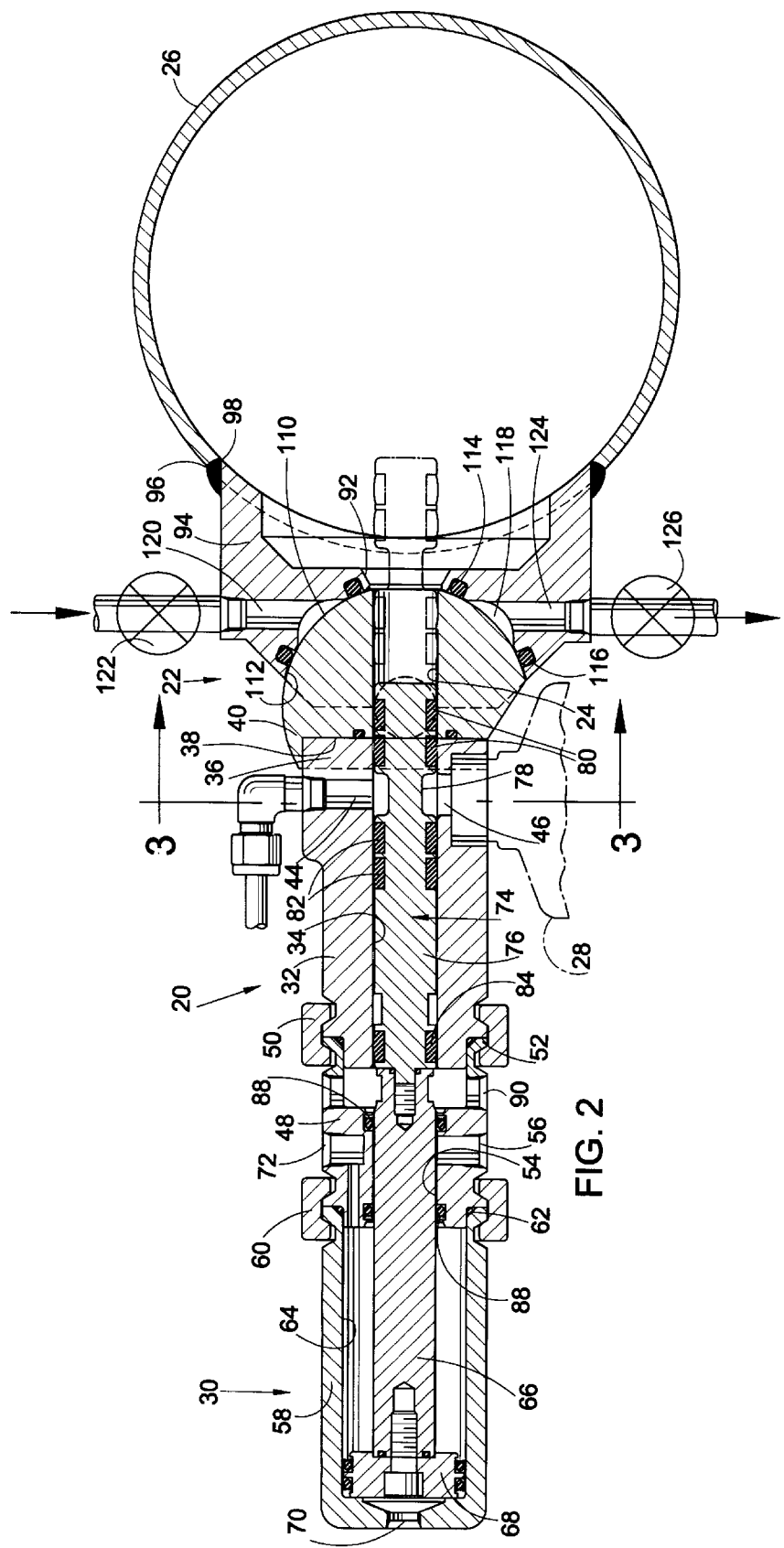
FIG. 2 is a cross sectional side elevation view of the sampler, showing a sample receiving plunger of the sampler in each of its sample receiving and sample delivering positions.

Referring to FIGS. 1 and 2, the sampler 20 includes a plunger in which there is an annular recess that is extendible into the pipe 26 for receiving in the recess a sample of liquid from the pipe, and that is then retractable from the pipe to carry the liquid sample in the recess to a point for collection of the sample, for example to a container 28. The recess is sized to receive and contain a precise volume of the liquid and the sampler may be periodically actuated so that the liquid samples collected in the container represent a composite sample of the liquid in the pipe. The plunger may be actuated by an electric motor or pneumatic motor means indicated generally at 30, at a rearward end of the sampler. A plurality of seals on the plunger maintain a liquid seal between the interior of the pipe and the sample collection point, and between the sample collection point and the motor means, during reciprocation of the plunger. In this manner, the sample is generally insensitive to the pressure of the liquid in the pipe and the collected sample is protected against contamination.

More specifically, the sampler 20 has a body 32 having a longitudinal bore 34. The bore 34 is of the same diameter as and axially aligned with the bore 24 in the connecting device 22. A forward end 36 of the body is received in a recess 38 in a rearward end of a movable valve member 40 of the connecting device 22 and is removably attached to the valve member by fasteners 42. Inlet and outlet ports 44 and 46 in the body intercept the bore 34 at the sample collection point.

A head 48 is attached to the rearward end of the sampler body 32 by a quick release clamp 50 and is sealed to the body by an O-ring seal 52. A bore 54 through the head is in axial alignment with the bores 34 and 24, and a drain port 56 intersects the bore. The motor means 30 may comprise a pneumatic motor means having a cylinder 58 connected to a rearward end of the head by a quick release clamp 60 and sealed to the head by an O-ring seal 62. The pneumatic cylinder has a bore 64 axially aligned with the bores 54, 34 and 24, and a cylinder rod 66 is reciprocated by a piston 68 in the cylinder bore. The piston and cylinder rod are moved in a forward or rightward direction by air under pressure at an air inlet 70 and are moved rearward or leftward by air under pressure at an air inlet 72.

Extending through the bores 34 and 24 is a plunger assembly, indicated generally at 74. The plunger assembly includes a plunger 76 in which is formed an annular recess or sample chamber 78 of predetermined volume. A pair of annular seals 80 are on the plunger forwardly of the sample chamber and a pair of annular seals 82 are on the plunger rearwardly of the sample chamber. An annular seal 84 is on a rearward end of the plunger and wrench flats 86 are formed on the plunger just forward of the seal 84. A forward end of the motor means cylinder rod 66 is threaded to a rearward end of the plunger, so that actuation of the motor means 30 reciprocates the plunger assembly 74 within the bores 34 and 24. A pair of ring seals 88 seal the cylinder rod 66 to the head bore 54.

The plunger assembly 74 and cylinder rod 66 are of a slightly smaller diameter than the diameter of the bores 54, 34 and 24 within which they reciprocate. In consequence, the seals carried by the plunger assembly and cylinder rod control the concentricity of the same within the bores and function as bearings to enable them to reciprocate easily. This prevents direct sliding contact between the relatively hard components of the sampler, whereby the life of the sampler is extended and its repair frequency reduced.

In operation of the liquid sampler 20, the seals 80 and 82 maintain a liquid seal between the inlet and outlet ports 44 and 46 and the liquid in the pipe 26. In addition, the seals 80, 82 and 84 wipe the bores 24 and 34 clean of sampled liquid with each reciprocation of the plunger assembly and prevent liquid from moving behind the seal 84. To prevent an accumulation of any liquid that might leak past the seal 84, the head 48 has a drain port 90.

With the sampler body bore 34 and the movable valve member bore 24 in axial alignment with each other and with an opening or aperture 92 in a body 94 of the connecting device 22 that communicates with the interior of the pipe 26, the pneumatic motor means 30 may be actuated to extend the plunger assembly 74 forwardly into the pipe. Upon forward movement of the plunger assembly through the bores 34 and 24 and the aperture 92 to extend the annular sample chamber 78 into the liquid in the pipe, the seal 84 moves from the rearward end of the bore 34 to adjacent the inlet and outlet ports 44 and 46 to squeegee and wipe the bore clean of any liquid that might be behind the seals 82, and the seals 82 move from behind the ports to adjacent the front of the valve member bore 24 to wipe the bores 34 and 24 forwardly of the ports. In this manner, the bores 34 and 24 are cleaned of any accumulated liquid with each reciprocation of the plunger assembly.

As the plunger assembly 74 is extended rightward and forward, the seals 82 form a liquid seal with the valve member bore 24 forward of the inlet and outlet ports 44 and 46 before the seals 80 move out of the bore 24. Similarly, upon leftward movement and retraction of the plunger assembly, the seals 80 enter the bore 24 before the seals 82 move rearward of and expose the ports. En consequence, a liquid seal is at all times maintained between the liquid in the pipe 26 and the inlet and outlet ports, and only the liquid sample in the sample chamber 78 ever reaches the ports.

Upon extending the plunger assembly 74 forward to obtain a sample of liquid, the sample chamber 78 is projected into the pipe 26 and exposed to the stream of liquid flowing through the pipe. The sample chamber is therefore washed by the product stream upon each cycle of operation of the sampler. This minimizes an accumulation of product in the chamber and the annular shape of the chamber and its direct exposure to the product stream help to prevent it from becoming clogged by solids. The sample collecting chamber is therefore self-cleaning of debris that may be encountered in product lines, so that when it is withdrawn into the sampler bore, it will carry a true sample of the liquid flowing through the pipe.

Upon the plunger assembly 74 being fully retracted, the annular recess or sample chamber 78 is positioned at the outlet port 46, so that the liquid sample in the recess may pass through the outlet port for immediate analysis or collection in the container 28. To facilitate removal of the sample from the recess in the case of high viscosity or thixotropic materials, a stream of air or other suitable fluid can be introduced through the inlet port 44 to flush or blow the sample from the recess, or vacuum can be applied to the outlet port. This enables substantially any type of liquid to readily be ejected from the sample chamber.

The body 94 of the connecting device 22 is welded at 96 to the pipe 26 around the periphery of an aperture 98 in the pipe. The movable valve member or selector member 40 is rotatable relative to the body 94 by means of a pair of trunnions 100 formed on opposite sides of the valve member and rotatably received in a pair of clamps 102 attached to the body by fasteners 104. The body is cup-shaped and extends around the forward end of the valve member, and clamp collars 106 and 108 on opposite trunnions are adjusted to control side to side movement of the valve member 40. The valve member has a spherical surface 110 at least forwardly of the forward end 36 of the sampler body 32, and the connecting device body 94 has a generally spherical surface 112 that faces and conforms to the spherical surface of the valve member. A pair of ring seals 114 and 116 in annular recesses in the spherical surface of the body maintain a liquid seal between the valve member and the body, with the valve member floating and being rotatable on the seals out of contact with the body. The spherical surface 112 of the body is relieved by an annular recess 118 between the seals 114 and 116, and an upper inlet passage 120 valved at 122, and a lower outlet passage 124 valved at 126, extend through the body in communication with the annular recess 118.

In FIGS. 1 and 2 the movable selector or valve member 40 is shown positioned to accommodate operation of the liquid sampler 20 to obtain samples of liquid from within the pipe 26. The outlet from the valve member bore 24 is axially aligned with the opening 92 in the connecting device body 94 and with the aperture 98 in the pipe. Consequently, when the sampler plunger assembly 74 is moved forwardly by the motor means 30, the forward end of the plunger assembly is extended into the pipe (as shown in phantom lines) to receive a liquid sample within the sample receiving recess 78. Retraction of the plunger assembly then delivers the sample within the recess to the collection point between the inlet port 44 and outlet port 46. At all times during operation of the sampler, the seals 80 and 82 maintain a seal between the interior of the pipe and the collection point.

The invention contemplates that the connecting device valve member 40 be rotatable to a position where the valve member bore 24, and therefore the sampler 20, are placed out of communication with and isolated from the aperture 92 in the body 94, and therefore out of communication with and isolated from the pipe aperture 98 and the liquid in the pipe 26. With the sampler plunger assembly 74 retracted, the sampler and the connecting device movable valve member 40 may be rotated about the trunnions 100 to bring the valve member to the position shown in FIG. 4. In this orientation of the valve member, the outlet from the bore 24 opens to the annular recess 118 toward the outlet passage 124 and is out of communication with the liquid in the pipe. A flow of liquid from the pipe through the aperture 92 is then prevented by the surface 110 of the valve member and the ring seal 114, while at the same time the ring seal 114 serves to isolate the inlet to the valve member bore 24 from the aperture 92 and the liquid in the pipe. The sampler 20 can then be disconnected and separated from the valve member for maintenance, repair or replacement without occurrence of an uncontrolled escape of liquid from the pipe through the bore 24 and without any need to disturb or interrupt the flow of liquid in the pipe.

It is desirable that the valve member 40 be locked in place both when it is positioned as in FIGS. 1 and 2 and when it is positioned as in FIG. 4, to prevent it from inadvertently being rotated from its intended position. For the purpose, as shown in FIG. 5 the clamp collar 108 is keyed at 128 to the trunnion 100 for conjoint rotation with the valve member. The clamp collar 108 is in the position shown in solid lines in FIG. 5 when the valve member is positioned as in FIG. 2, but rotates with the trunnion and moves to the position shown in phantom lines in FIG. 5 and against a stop 129 when the valve member is rotated to the position shown in FIG. 4. In either position, the clamp collar may be locked in place by a removable and reinsertable lock screw 130 to prevent accidental rotation of the valve member.

In a contemplated procedure to remove the sampler 20 from the connecting device 22 for repair or replacement, the sampler plunger assembly 74 is retracted and its motor means 30 is deactivated. The outlet valve 126, which normally is open to provide a drain for any liquid leaking past the ring seal 114, is then closed and the sampler is unlocked, tilted from its position in FIG. 2 to its position in FIG. 4, and then locked in place. The inlet and outlet valves 122 and 126 are then opened so that a solvent at the inlet valve flows through and cleans the connecting device annular recess 118, following which the inlet valve is closed and the solvent allowed to drain from the annular recess through the outlet valve. The sampler is then detached from the connecting device, by removal of the fasteners 104, for repair, remanufacture or replacement, following which it is reattached to the connecting device. The outlet valve 126 is then closed; the connecting device is unlocked, rotated to the operative position and then relocked; and the inlet and outlet valves are again opened to flush the annular recess 118. The inlet valve is then closed and the sampler motor means 30 is again actuated to return the sampler to operation.

The connecting device 22 has some similarity to the connecting device shown in FIG. 1 of aforementioned U.S. Pat. No. 4,628,732, the teachings of which have been specifically incorporated herein by reference. That connecting device is used to support a measuring instrument that measures properties of a process such as the temperature, the density, the pH-value, the consistency or some other characteristic of the process, but that does not and cannot remove discrete samples of the process itself from a main body of the process. Said patent also discloses various other arrangements of connecting devices for a measuring instrument, at least some of which could be adapted for use in an apparatus embodying the teachings of the present invention. The primary criteria to be satisfied by any such connecting device is that it be both capable of releasably carrying the liquid sampler and movable between a position placing the sampler into communication with the interior of a vessel to accommodate operation of the sampler to obtain samples of liquid from the vessel and a position placing the sampler out of communication with the interior of the vessel so that the sampler can be disconnected from the connecting device for replacement, maintenance or repair, without allowing liquid to escape from the vessel.

While embodiments of the invention have been described in detail, various modifications and other embodiments thereof can be devised by one skilled in the art without departing from the spirit and scope of the invention, as defined in the accompanying claims.

What is claimed is:

1. A sampling apparatus, comprising:

a liquid sampler operable to obtain discrete samples of liquid from a body of liquid in a vessel;

a connecting device for coupling said liquid sampler to the vessel at an aperture in the vessel, wherein said liquid sampler is releasably attached to said connecting device and said connecting device is operable between a first position placing said liquid sampler into communication with the liquid in the vessel through the aperture and a second position placing said liquid sampler out of communication with the aperture and the liquid in the vessel, said liquid sampler being detachable from said connecting device, without an escape of liquid from the vessel through said connecting device, when said connecting device is in said second position, wherein said connecting device has a bore therethrough, said sampler communicates with one end of said bore when said sampler is attached to said connecting device, an opposite end of said bore is in communication with the aperture in the vessel when said connecting device is in said first position and is out of communication with the aperture when said connecting device is in said second position, said connecting device includes a body having an opening therein for communication with the aperture to the vessel and a valve member carried by said body and movable relative thereto, and said valve member has said bore therethrough, and wherein said liquid sampler includes a plunger having a liquid sample receiving recess therein, said liquid sampler being operable, when said connecting device is in said first position, to extend said plunger and said recess therein through said valve member bore, said body opening and the aperture into the vessel to receive in said recess a sample of the liquid in the vessel, and to then retract said plunger and said recess therein from the vessel and through the aperture, said opening and said bore to deliver the liquid sample in said recess to a sample collection point, and including seal means for maintaining a liquid seal between the interior of the vessel and said sample collection point during extension and retraction of said plunger while said valve member is in said first position.

2. A sampling apparatus as in claim 1, wherein said liquid sampler is releasably attached to said valve member in communication with said one end of said bore, said valve member is movable to said first position to place said opposite end of said bore into communication with the aperture in the vessel and to said second position to place said opposite end of said bore out of communication with the aperture, and said liquid sampler is movable with said valve member.

3. A sampling apparatus as in claim 2, including seal means for sealing said valve member to said body to prevent leakage of liquid from the vessel through said body opening and between said body and valve member and out of said connecting device.

4. A sampling apparatus as in claim 1, wherein said liquid sampler has a housing and a bore in said housing in axial alignment with said connecting device bore, said sample collection point is in said housing bore, and said plunger is retracted into said housing bore to move said recess and the liquid sample therein to said sample collection point.

5. A sampling apparatus as in claim 4, including means in said housing at said sample collection point for receiving the liquid sample from said recess.

6. A sampling apparatus as in claim 4, wherein said seal means is on said plunger on opposite sides of said recess for maintaining a liquid seal between the interior of the vessel and said sample collection point during operation of said liquid sampler.

7. A sampling apparatus, comprising:

a liquid sampler including a housing having a bore therein and a plunger reciprocable in said bore, said plunger having a sample receiving recess therein intermediate its ends; and a connecting device including a movable valve having a bore extending therethrough, wherein said liquid sample is releasably attached to said connecting device valve at one end of said valve bore with said housing and valve bores in communication, said connecting device is for being coupled to a liquid containing vessel with an opposite end of said valve bore in communication with the liquid in the vessel through an aperture in the vessel, and said plunger is reciprocable in a forward direction to extend said plunger and said recess therein through said housing and valve bores and the vessel aperture into the liquid in the vessel to receive a liquid sample in said plunger recess, and then in a rearward direction to retract said plunger from the vessel and through the aperture in the vessel and said valve and housing bores to move said plunger recess and the liquid sample therein to a sample collection point in said housing bore, and wherein said valve is movable between a first position where said opposite end of its bore communicates with the vessel interior through the aperture and a second position where said opposite end of its bore is out of communication with the vessel interior and the aperture, and said liquid sampler further includes seal means for maintaining a liquid seal between the interior of the vessel and said sample collection point during reciprocation of said plunger while said valve is in said first position, and wherein movement of said valve to said second position enables said liquid sampler to be detached from said valve for maintenance, repair or replacement without escape of liquid from the vessel through said valve bore.

8. A sampling apparatus as in claim 7, including motor means for reciprocating said liquid sampler plunger.

9. A sampling apparatus as in claim 7, wherein said connecting device includes means for releasably locking said valve in either said first or second position.

10. A sampling apparatus, comprising:

a connecting device having a body attachable to a liquid containing vessel having an aperture thereto, said body having an opening for communication with the aperture and said connecting device further including a selector member sealed to and movable relative to said body and having a bore therethrough; and a liquid sampler releasably attached to said connecting device selector member in communication with one end of said selector member bore, said selector member being movable between a first position where an opposite end of said bore is in communication with said body opening and a second position where said opposite end of said bore is out of communication with said body opening, wherein when said selector member is in said first position said sampler can be extended through said selector member bore, said body opening and the vessel aperture into the liquid in the vessel to obtain a discrete sample of liquid, and can then be retracted to carry the discrete liquid sample through the vessel aperture, said body opening and said selector member bore to a sample collection point, and when said selector member is in said second position said liquid sampler can be disconnected therefrom for replacement, repair or maintenance without occurrence of an escape of liquid from the vessel, and wherein said liquid sampler includes a plunger having a liquid sample receiving chamber therein, means for reciprocating said plunger to move said plunger forwardly through said selector member bore and into the vessel to receive the discrete liquid sample in said chamber and to then move said plunger rearwardly out of the vessel and through said selector member bore to deliver said chamber and discrete liquid sample therein to a sample collection point, and seal means for maintaining a liquid seal between the interior of the vessel and the sample collection point during reciprocation of said plunger when said selector member is in said first position.

11. A sampling apparatus, comprising:

a liquid sampler including a housing having a bore therein, a plunger in said bore and having a sample receiving recess therein intermediate its ends, means for reciprocation said plunger in said bore, and seal means for sealing said plunger to said bore;

a connecting device including a movable valve having a bore extending therethrough, and means for releasably attaching said liquid sampler to said connecting device valve at one end of said valve bore with said housing and valve bores in communication, wherein said connecting device is for being coupled to a liquid containing vessel with an opposite end of said valve bore in communication with the liquid in the vessel through an aperture in the vessel, and said valve is movable between a first position where said opposite end of its bore communicates with the vessel interior through the aperture and a second position where said opposite end of its bore is out of communication with the vessel interior and the aperture, and wherein, when said valve is in said first position, said means for reciprocating reciprocates said plunger in a forward direction to extend said plunger and said recess therein through said housing and valve bores and the vessel aperture into the liquid in the vessel to receive a liquid sample in said recess, and then in a rearward direction to retract said plunger from the vessel and through the aperture in the vessel and said valve and housing bores to move said plunger recess and the liquid sample therein to a sample collection point in said housing bore, said liquid sampler seal means sealing said plunger to said housing and valve bores and maintaining a liquid seal between the interior of the vessel and the sample collection point during reciprocation of said plunger while said connecting device valve is in said first position.

12. A sampling apparatus, comprising:

a liquid sampler operable to obtain discrete samples of liquid from a body of liquid in a vessel; and a connecting device for coupling said liquid sampler to the vessel at an aperture in the vessel, wherein said liquid sampler is releasably attached to said connecting device and said connecting device is operable between a first position placing said liquid sampler into communication with the liquid in the vessel through the aperture and a second position placing said liquid sampler out of communication with the aperture and the liquid in the vessel, said liquid sampler being detachable from said connecting device, without an escape of liquid from the vessel through said connecting device, when said connecting device is in said second position, said liquid sampler including sampling means that is extendable, when said connecting device is in said first position, into the vessel through the aperture to obtain a sample of liquid from the vessel and is then retractable from the vessel through the aperture to carry the liquid sample to a sample collection point in said liquid sampler, and seal means for maintaining a liquid seal between the interior of the vessel and said sample collection point while said connecting device is in said first position.

\* \* \* \* \*